United States Patent
Hayashi et al.

(10) Patent No.: US 9,714,921 B2
(45) Date of Patent: *Jul. 25, 2017

(54) METHOD OF IDENTIFYING DIRECTION OF MULTILAYER CERAMIC CAPACITOR, APPARATUS IDENTIFYING DIRECTION OF MULTILAYER CERAMIC CAPACITOR, AND METHOD OF MANUFACTURING MULTILAYER CERAMIC CAPACITOR

(71) Applicant: MURATA MANUFACTURING CO., LTD., Kyoto-fu (JP)

(72) Inventors: Akihiro Hayashi, Nagaokakyo (JP); Minako Takahashi, Nagaokakyo (JP); Yoshikazu Sasaoka, Nagaokakyo (JP)

(73) Assignee: Murata Manufacturing Co., Ltd., Kyoto-fu (JP)

(*) Notice: Subject to any disclaimer, the term of this patent is extended or adjusted under 35 U.S.C. 154(b) by 49 days.

This patent is subject to a terminal disclaimer.

(21) Appl. No.: 14/729,994

(22) Filed: Jun. 3, 2015

(65) Prior Publication Data
US 2015/0377833 A1    Dec. 31, 2015

(30) Foreign Application Priority Data

Jun. 25, 2014   (JP) .................. 2014-130591
Jun. 25, 2014   (JP) .................. 2014-130592
Mar. 24, 2015   (JP) .................. 2015-061651

(51) Int. Cl.
*G01R 33/04*   (2006.01)
*G01R 33/07*   (2006.01)
*G01N 27/72*   (2006.01)

(52) U.S. Cl.
CPC ................... *G01N 27/72* (2013.01)

(58) Field of Classification Search
CPC ...... G01R 33/04; G01R 33/07; G01R 33/072; G01R 33/1215; G01R 33/1253;
(Continued)

(56) References Cited

U.S. PATENT DOCUMENTS 5,153,876 A   10/1992   Sin
6,194,864 B1   2/2001   Kinpara et al.
(Continued)

FOREIGN PATENT DOCUMENTS

CN   203631319 U   6/2014
JP   H07-115034 A   5/1995
(Continued)

OTHER PUBLICATIONS

An Office Action issued by the Korean Patent Office on May 3, 2016, which corresponds to Korean Patent Application No. 10-2015-0069597 and is related to U.S. Appl. No. 14/729,994; with English language translation.

*Primary Examiner* — Bot Ledynh
*Assistant Examiner* — Taqi Nasir
(74) *Attorney, Agent, or Firm* — Studebaker & Brackett PC

(57) ABSTRACT

A method of identifying a direction of a multilayer ceramic capacitor includes the steps of transporting a plurality of multilayer ceramic capacitors in one line before each of a magnetism generator and a magnetic flux density measurement instrument, measuring a magnetic flux density with the magnetic flux density measurement instrument at the time when each of the plurality of multilayer ceramic capacitors passes before the magnetic flux density measurement instrument, and identifying a direction of stack of the multilayer ceramic capacitors based on the magnetic flux density measured in the step of measuring a magnetic flux density.

8 Claims, 15 Drawing Sheets

(58) Field of Classification Search
CPC .. G01R 33/1276; G01R 15/04; G01R 15/148;
G01R 15/22; G01R 15/245; G01R
19/0084; G01R 19/10; G01R 19/16523;
G01R 1/00; G01R 1/06705; G01R 21/08;
G01R 22/061
USPC ....... 324/228, 328, 519, 750.17, 548, 76.66,
324/331, 345, 381, 463, 219, 246,
324/259–263, 529, 750.12, 754.17
See application file for complete search history.

(56) References Cited

U.S. PATENT DOCUMENTS

| | | | |
|---|---|---|---|
| 6,650,113 B2* | 11/2003 | Sekiya | G01R 33/028 324/207.17 |
| 8,797,708 B2* | 8/2014 | Sakuratani | H01L 41/0471 361/303 |
| 9,431,175 B2* | 8/2016 | Sasaoka | H01G 4/012 |
| 2002/0023506 A1 | 2/2002 | Miyamoto | |
| 2003/0179151 A1 | 9/2003 | Senba et al. | |
| 2003/0227363 A1* | 12/2003 | Leisten | H01F 3/14 336/178 |
| 2004/0208032 A1 | 10/2004 | Edo et al. | |
| 2005/0062466 A1 | 3/2005 | Miyamoto | |
| 2005/0167243 A1* | 8/2005 | Yagi | B65G 27/02 198/381 |
| 2006/0250747 A1* | 11/2006 | Takashima | H01G 4/12 361/272 |
| 2009/0179810 A1* | 7/2009 | Kato | G06K 7/10178 343/785 |
| 2011/0089942 A1* | 4/2011 | Goodwill | A61B 5/05 324/301 |
| 2012/0119698 A1 | 5/2012 | Karalis et al. | |
| 2014/0126106 A1 | 5/2014 | Sawada | |
| 2014/0182101 A1* | 7/2014 | Sasaoka | H01G 4/012 29/25.41 |
| 2015/0116901 A1 | 4/2015 | Sasaoka | |

FOREIGN PATENT DOCUMENTS

| | | |
|---|---|---|
| JP | H07-115033 B2 | 12/1995 |
| JP | 2002-029627 A | 1/2002 |
| JP | 2005-217136 A | 8/2005 |
| JP | 2014-130912 A | 7/2014 |
| TW | 531976 B | 5/2003 |
| TW | 200540885 A | 12/2005 |

* cited by examiner

METHOD OF IDENTIFYING DIRECTION OF MULTILAYER CERAMIC CAPACITOR, APPARATUS IDENTIFYING DIRECTION OF MULTILAYER CERAMIC CAPACITOR, AND METHOD OF MANUFACTURING MULTILAYER CERAMIC CAPACITOR

CROSS REFERENCE TO RELATED APPLICATIONS

This application claims benefit of priority to Japanese Patent Application No. 2014-130591 filed on Jun. 25, 2014, Japanese Patent Application No. 2014-130592 filed on Jun. 25, 2014, and Japanese Patent Application No. 2015-061651 filed on Mar. 24, 2015, the entire content of each of which is incorporated herein by reference.

TECHNICAL FIELD

The present disclosure relates to a method of identifying a direction of a multilayer ceramic capacitor, an apparatus identifying a direction of a multilayer ceramic capacitor, and a method of manufacturing a multilayer ceramic capacitor.

BACKGROUND

A multilayer ceramic capacitor has a plurality of internal electrodes stacked along one direction. Therefore, there is a demand that identification of a direction of stack of internal electrodes in a multilayer ceramic capacitor is desired. For example, in a case that a multilayer ceramic capacitor has a square prismatic shape, however, it is difficult to identify a direction of stack of internal electrodes in a multilayer ceramic capacitor based on appearance.

For example, Japanese Patent Laying-Open No. 7-115033 describes a method allowing identification of a direction of stack of internal electrodes in a multilayer ceramic capacitor not based on appearance. Specifically, Japanese Patent Laying-Open No. 7-115033 describes a method of identifying a direction of an internal electrode layer based on intensity of magnetization by applying certain magnetic field to one surface from which an internal electrode layer is not extracted and by measuring a magnetic flux density of a multilayer ceramic capacitor. This method makes use of a difference in measured magnetic flux density between a state that a capacitor is arranged in an orientation in which an internal electrode is substantially in parallel to a magnetic flux (an internal electrode is perpendicular to a bottom surface as a capacitor) and a state that a capacitor is arranged in an orientation in which an internal electrode is substantially perpendicular thereto (an internal electrode is horizontal to the bottom surface as a capacitor).

A difference in measured magnetic flux density, however, is very small between a case that a direction of stack of internal electrodes and a direction of a magnetic flux are in parallel to each other and a case that a direction of stack of internal electrodes and a direction of a magnetic flux are perpendicular to each other. In addition, a measured magnetic flux density is significantly dependent on positional relation among a magnet, a sensor probe, and a capacitor. In particular, in a multilayer ceramic capacitor small in size, influence by positional relation among a magnet, a sensor probe, and a capacitor on a measured magnetic flux density is great.

Thus, since a difference in magnetic flux density measured at the time when a direction of stack is different is small and a measured magnetic flux density is significantly different depending on a position of a capacitor at the time of measurement, it is difficult to accurately identify a direction of stack of a multilayer ceramic capacitor with the method described in Japanese Patent Laying-Open No. 7-115033.

This problem will more specifically be described. For example, a case that a magnetic flux density of a multilayer ceramic capacitor having a length dimension of 1 mm, a width dimension of 0.5 mm, and a height dimension of 0.5 mm and having a capacitance of 4.7 µF is measured under a certain measurement condition is assumed. A maximum magnetic flux density of this multilayer ceramic capacitor in a case that a direction of stack of internal electrodes is in parallel to a direction of a magnetic flux is approximately 53.6 mT. On the other hand, a maximum magnetic flux density of this multilayer ceramic capacitor in a case that a direction of stack of internal electrodes is perpendicular to a direction of a magnetic flux is approximately 52.3 mT. Therefore, a difference in maximum value for a magnetic flux density of this multilayer ceramic capacitor between a case that a direction of stack of internal electrodes and a direction of a magnetic flux are in parallel to each other and a case that they are perpendicular to each other is only 1.3 mT. Therefore, a difference in maximum value for a magnetic flux density between the case that the direction of stack of internal electrodes and the direction of the magnetic flux are in parallel to each other and a case that they are perpendicular to each other is only 2.4% as compared to the maximum value for the magnetic flux density in the case that the direction of stack of the internal electrodes and the direction of the magnetic flux are in parallel to each other.

A magnetic flux density of a multilayer ceramic capacitor in which a direction of stack of internal electrodes and a direction of a magnetic flux are in parallel to each other at the time when a position of measurement in a multilayer ceramic capacitor is displaced by 0.3 mm from a central position of the multilayer ceramic capacitor is approximately 52.3 mT, which is substantially equal to the maximum value for the magnetic flux density of the multilayer ceramic capacitor in the case that the direction of stack of the internal electrodes and the direction of the magnetic flux are perpendicular to each other (a case that a measurement position is located at a central position of the multilayer ceramic capacitor). Thus, when a measurement position in a multilayer ceramic capacitor may vary by 0.3 mm or greater, identification of a direction of a multilayer ceramic capacitor is difficult. This problem is noticeable because it is more difficult to set a measurement position to a central position as a multilayer ceramic capacitor is smaller in size, for example, when each dimension is smaller than a length dimension of 1 mm, a width dimension of 0.5 mm, and a height dimension of 0.5 mm.

With the method described in Japanese Patent Laying-Open No. 7-115033, a magnetism generator and a magnetic sensor should be arranged to be opposed to each other, with a capacitor lying therebetween. Therefore, the method described in Japanese Patent Laying-Open No. 7-115033 is restricted in terms of arrangement of the magnetism generator and the magnetic sensor. Therefore, the apparatus identifying a direction of a capacitor described in Japanese Patent Laying-Open No. 7-115033 is disadvantageous in low degree of freedom in design of an apparatus.

SUMMARY

A primary object of the present disclosure is to provide a method allowing accurate identification of a direction of a multilayer ceramic capacitor.

A method of identifying a direction of a multilayer ceramic capacitor based on the present disclosure is a method of identifying a direction of stack of a multilayer ceramic capacitor including a plurality of stacked internal electrodes. The method of identifying a direction of a multilayer ceramic capacitor includes the steps of transporting a plurality of multilayer ceramic capacitors in one line before each of a magnetism generator and a magnetic flux density measurement instrument, measuring a magnetic flux density with the magnetic flux density measurement instrument at the time when each of the plurality of multilayer ceramic capacitors passes before the magnetic flux density measurement instrument, and identifying the direction of stack based on the magnetic flux density measured in the step of measuring a magnetic flux density.

In one form of the present disclosure, in the step of identifying a direction of stack, an integral value of the magnetic flux density is calculated based on the magnetic flux density measured in the step of measuring a magnetic flux density and the direction of stack is identified based on the integral value of the magnetic flux density.

In one form of the present disclosure, the magnetism generator and the magnetic flux density measurement instrument are opposed to each other. In the step of measuring a magnetic flux density, the magnetic flux density measurement instrument measures a density of a magnetic flux generated from the magnetism generator at the time when each of the plurality of multilayer ceramic capacitors passes between the magnetism generator and the magnetic flux density measurement instrument.

In one form of the present disclosure, the magnetism generator is arranged upstream of the magnetic flux density measurement instrument in a direction of transportation of the plurality of multilayer ceramic capacitors. Before the step of measuring a magnetic flux density, the step of magnetizing each of the plurality of multilayer ceramic capacitors is further included.

In one form of the present disclosure, in the step of transporting a plurality of multilayer ceramic capacitors, the plurality of multilayer ceramic capacitors are transported to pass through a linear transportation path. In the step of measuring a magnetic flux density, the magnetic flux density measurement instrument measures the magnetic flux density at the time when the plurality of multilayer ceramic capacitors pass before the magnetic flux density measurement instrument as the plurality of multilayer ceramic capacitors pass through the linear transportation path.

In one form of the present disclosure, in the step of transporting a plurality of multilayer ceramic capacitors, the plurality of multilayer ceramic capacitors are transported while the plurality of multilayer ceramic capacitors are accommodated in a plurality of accommodation portions provided along an outer circumference of an annular rotor, respectively. In the step of measuring a magnetic flux density, the magnetic flux density measurement instrument measures the magnetic flux density at the time when the plurality of multilayer ceramic capacitors pass before the magnetic flux density measurement instrument while the plurality of multilayer ceramic capacitors are accommodated in the plurality of accommodation portions, respectively.

In one form of the present disclosure, in the step of transporting the plurality of multilayer ceramic capacitors, the plurality of multilayer ceramic capacitors are transported while the plurality of multilayer ceramic capacitors are accommodated in a plurality of cavities, respectively, which are provided in a taping. In the step of measuring a magnetic flux density, the magnetic flux density measurement instrument measures the magnetic flux density at the time when the plurality of multilayer ceramic capacitors pass before the magnetic flux density measurement instrument while the plurality of multilayer ceramic capacitors are accommodated in the plurality of cavities, respectively.

A method of manufacturing a series of multilayer ceramic capacitors based on the present disclosure includes the steps of identifying the direction of stack with the method of identifying a direction of a multilayer ceramic capacitor described in any portion above and accommodating a plurality of multilayer ceramic capacitors identical in the direction of stack in a plurality of cavities provided in a taping, respectively.

According to the present disclosure, a method allowing accurate identification of a direction of a multilayer ceramic capacitor can be provided.

The foregoing and other objects, features, aspects and advantages of the present disclosure will become more apparent from the following detailed description of the present disclosure when taken in conjunction with the accompanying drawings.

BRIEF DESCRIPTION OF THE DRAWINGS

Figure 1:
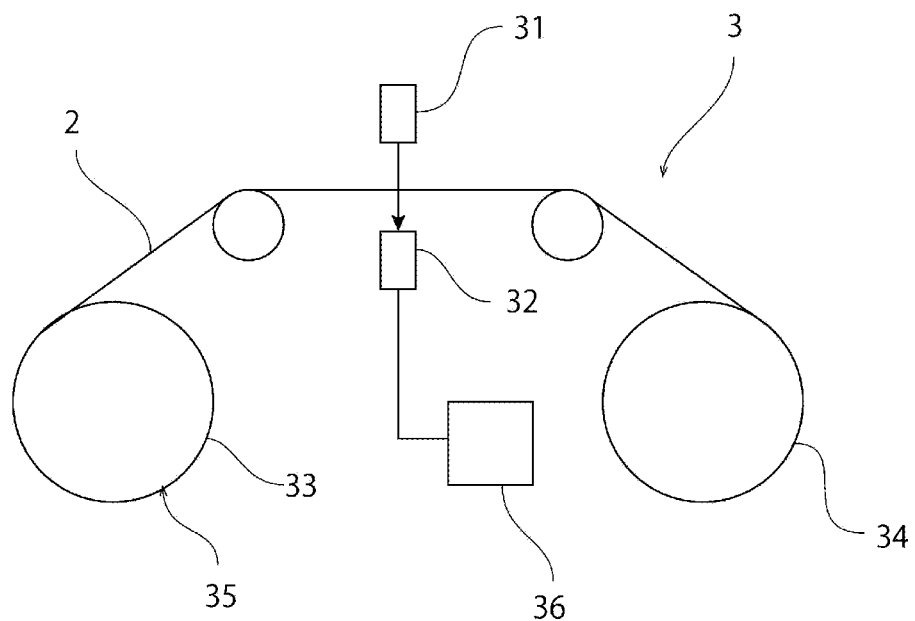
FIG. 1 is a schematic side view of an apparatus identifying a direction of a multilayer ceramic capacitor in a first embodiment of the present disclosure.

Each embodiment of the present disclosure will be described hereinafter with reference to the drawings. An embodiment below is merely an illustration. The present disclosure is not limited to an embodiment below.

In each drawing referred to in an embodiment, members having substantially the same function will be referred to by the same reference characters. A drawing referred to in an embodiment is schematic. A scale or the like of a dimension of an object drawn in the drawings may be different from a scale or the like of a dimension of an actual object. A scale or the like of a dimension of an object may be different between the drawings. A specific scale or the like of a dimension of an object should be determined with reference to the description below.

First Embodiment

In the present embodiment, a method of identifying a direction of a multilayer ceramic capacitor 1 shown in FIGS. 4 and 5 will be described. Initially, a construction of multilayer ceramic capacitor 1 which is an object of identification will be described.

Construction of Multilayer Ceramic Capacitor 1

Figure 4:
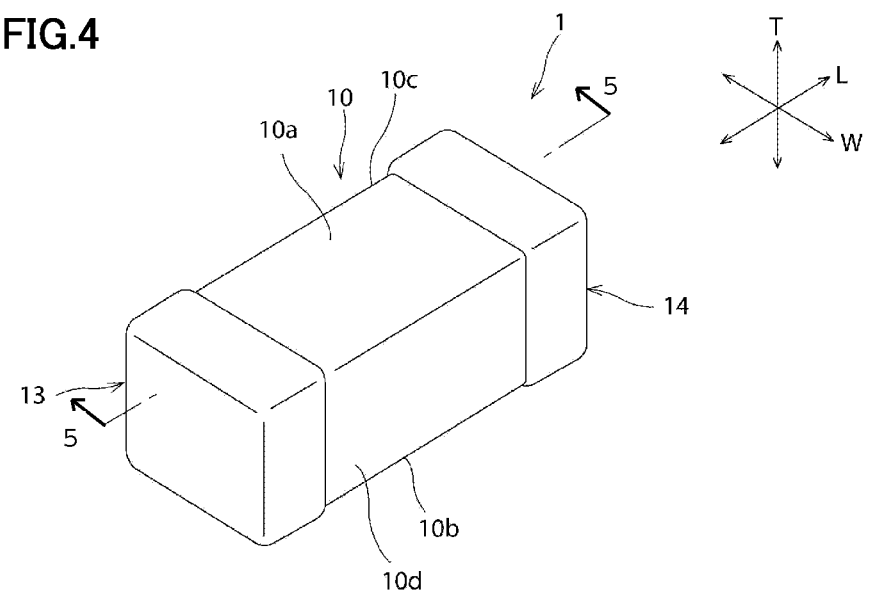
FIG. 4 is a simplified perspective view of the multilayer ceramic capacitor in the first embodiment of the present disclosure.
Figure 5:
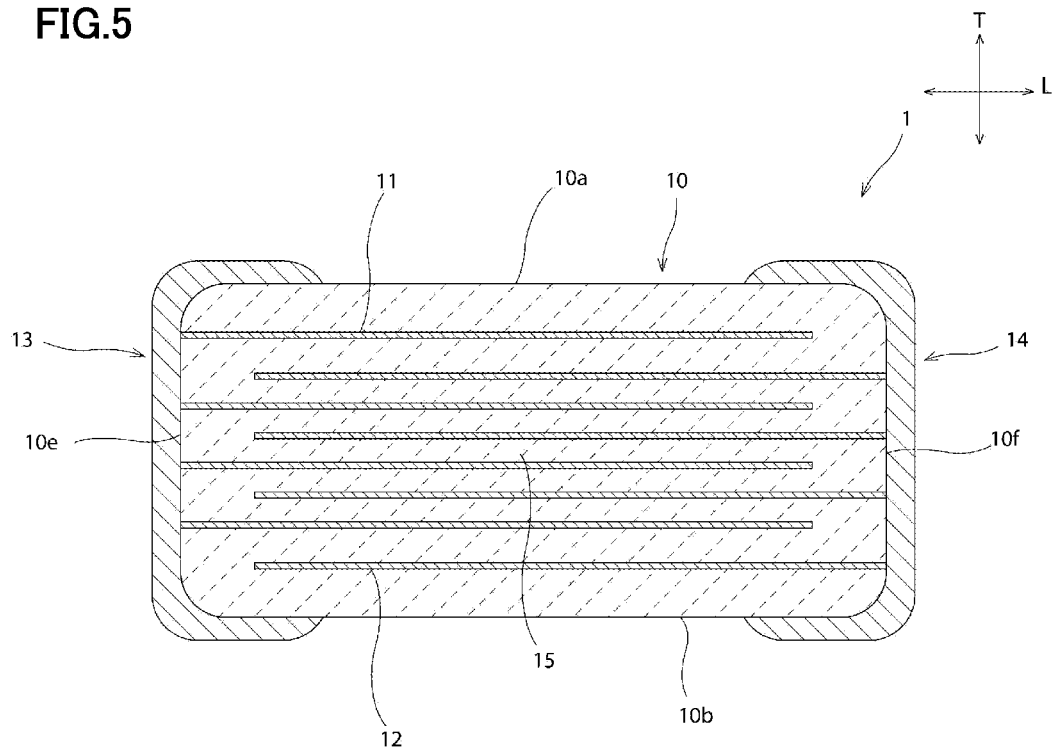
FIG. 5 is a simplified cross-sectional view along the line 5-5 in FIG. 4.

As shown in FIGS. 4 and 5, multilayer ceramic capacitor 1 includes a ceramic body 10. Ceramic body 10 is in a shape of a substantial parallelepiped. Specifically, ceramic body 10 is in a square prismatic shape. Ceramic body 10 has first and second main surfaces 10a and 10b, first and second side surfaces 10c and 10d, and first and second end surfaces 10e and 10f (see FIG. 5). Each of first and second main surfaces 10a and 10b extends along a length direction L and a width direction W. First main surface 10a and second main surface 10b are in parallel to each other. Each of first and second side surfaces 10c and 10d extends along length direction L and a thickness direction T. First side surface 10c and second side surface 10d are in parallel to each other. Each of first and second end surfaces 10e and 10f extends along width direction W and thickness direction T. First end surface 10e and second end surface 10f are in parallel to each other.

Ceramic body 10 has a dimension along length direction L preferably not smaller than 0.4 mm and not greater than 2.0 mm and more preferably not smaller than 0.6 mm and not greater than 1.0 mm Ceramic body 10 has a dimension along width direction W preferably not smaller than 0.2 mm and not greater than 1.2 mm and more preferably not smaller than 0.3 mm and not greater than 0.5 mm Ceramic body 10 has a dimension along thickness direction T preferably not smaller than 0.2 mm and not greater than 1.2 mm and more preferably not smaller than 0.3 mm and not greater than 0.5 mm. The reason why preferably the dimension along length direction L is not greater than 1.0 mm and the dimension along width direction W and thickness direction T is not greater than 0.5 mm is because in particular a position where a magnetic flux density is measured tends to vary from a central position of a multilayer ceramic capacitor in a case of a small product having a size equal to or smaller than such a size. The reason why preferably the dimension along length direction L is not smaller than 0.6 mm and each of the dimensions along the width direction W and the dimension along thickness direction T is not smaller than 0.3 mm is because identification of a direction based on a magnetic flux density is easier in a capacitor higher in density of internal electrodes. For similar reasons, a multilayer ceramic capacitor having a capacitance not lower than 1 µF is suitable for the present disclosure.

Ceramic body 10 can be composed, for example, of a material mainly composed of dielectric ceramics. Specific examples of dielectric ceramics include $BaTiO_3$, $CaTiO_3$, $SrTiO_3$, or $CaZrO_3$. To ceramic body 10, for example, at least one sub component such as an Mn compound, an Mg compound, an Si compound, a Co compound, an Ni compound, and a rare-earth compound may be added as appropriate.

A "substantial parallelepiped" includes a parallelepiped of which a corner portion or ridge line portion is beveled and a parallelepiped of which corner portion or ridge line portion is rounded.

As shown in FIG. 5, a plurality of internal electrodes 11 and 12 are provided in ceramic body 10. The plurality of internal electrodes 11 and 12 are stacked along thickness direction T. Each of internal electrodes 11 and 12 is provided in parallel to length direction L and width direction W. In ceramic body 10, internal electrode 11 and internal electrode 12 are alternately provided along thickness direction T. A ceramic portion 15 is arranged between internal electrode 11 and internal electrode 12 adjacent in thickness direction T. Namely, internal electrode 11 and internal electrode 12 adjacent in thickness direction T are opposed to each other with ceramic portion 15 being interposed.

Internal electrode 11 is extended from first end surface 10e. An external electrode 13 is provided on first end surface 10e. External electrode 13 is electrically connected to internal electrode 11. Internal electrode 12 is extended from second end surface 10f. An external electrode 14 is provided on second end surface 10f. External electrode 14 is electrically connected to internal electrode 12. Internal electrodes 11 and 12 can be composed of such a magnetic material as Ni. External electrodes 13 and 14 can be composed, for example, of an appropriate conductive material such as Ni, Cu, Ag, Pd, Au, or an alloy.

Figure 2:
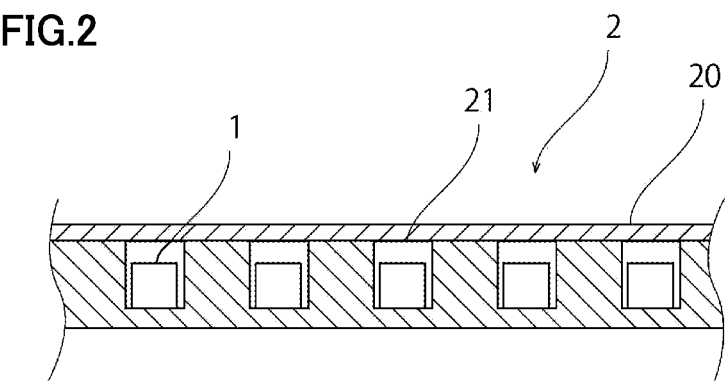
FIG. 2 is a simplified cross-sectional view of a series of multilayer ceramic capacitors in the first embodiment of the present disclosure.
Figure 3:
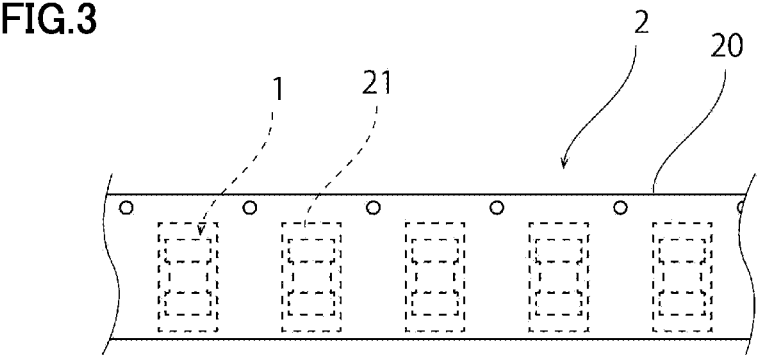
FIG. 3 is a simplified plan view of the series of multilayer ceramic capacitors in the first embodiment of the present disclosure.

As shown in FIGS. 2 and 3, multilayer ceramic capacitor 1 constitutes a series of multilayer ceramic capacitors 2. The series of multilayer ceramic capacitors 2 has taping 20. Taping 20 has a plurality of accommodation chambers 21 in a parallelepiped shape provided at an interval along a longitudinal direction. The plurality of accommodation chambers 21 accommodate multilayer ceramic capacitors 1, respectively. In a plan view, accommodation chamber 21 is larger than multilayer ceramic capacitor 1. Therefore, multilayer ceramic capacitor 1 can displace in a direction along a surface in accommodation chamber 21. When a position of multilayer ceramic capacitor 1 in accommodation chamber 21 varies for each accommodation chamber 21, an amount of variation from a central position of the multilayer ceramic capacitor in measurement of a magnetic flux density also varies for each accommodation chamber 21.

Stack ceramic capacitor 1 may be a three-terminal or a multiple-terminal multilayer ceramic capacitor including a side-surface electrode in addition to a two-terminal multilayer ceramic capacitor as shown in FIG. 4.

Construction of Apparatus 3 Identifying Direction of Multilayer Ceramic Capacitor An apparatus 3 identifying a direction of a multilayer ceramic capacitor is an apparatus for identifying a direction of stack of a plurality of internal electrodes 11 and 12 in multilayer ceramic capacitor 1. A "direction of stack of a plurality of internal electrodes 11 and 12 in multilayer ceramic capacitor 1" herein will hereinafter be referred to as a "direction of stack of multilayer ceramic capacitor 1" or simply as a "direction of stack."

As shown in FIG. 1, direction identification apparatus 3 includes a magnetism generator 31 and a magnetic flux density measurement instrument 32. Magnetic flux density measurement instrument 32 is arranged to be able to detect a density of a magnetic flux generated by magnetism generator 31. Magnetic flux density measurement instrument 32 measures a density of a magnetic flux generated from magnetism generator 31. Specifically, magnetic flux density measurement instrument 32 successively measures a magnetic flux density at an interval approximately not less than 10 kHz and not more than 100 kHz.

Direction identification apparatus 3 further includes a transportation apparatus 35. Transportation apparatus 35 has multilayer ceramic capacitors 1 pass between magnetism generator 31 and magnetic flux density measurement instrument 32. Specifically, transportation apparatus 35 has a first roll 33 and a second roll 34. The series of multilayer ceramic capacitors 2 is wound around first roll 33 and the series of multilayer ceramic capacitors 2 is fed from this first roll 33. The series of multilayer ceramic capacitors 2 which has passed between magnetism generator 31 and magnetic flux density measurement instrument 32 is wound up around second roll 34.

Magnetic flux density measurement instrument 32 measures a magnetic flux density at least when multilayer ceramic capacitor 1 passes before magnetic flux density measurement instrument 32. Magnetic flux density measurement instrument 32 outputs a result of measurement to a direction identification portion 36. Direction identification portion 36 identifies a direction of stack of multilayer ceramic capacitor 1 based on the result of measurement of the magnetic flux density output from magnetic flux density measurement instrument 32. Direction identification portion 36 successively identifies this direction of stack of a plurality of multilayer ceramic capacitors 1 which are arranged in one line at an interval from one another in the series of multilayer ceramic capacitors 2.

In manufacturing the series of multilayer ceramic capacitors 2, initially, multilayer ceramic capacitor 1 is fabricated. Then, fabricated multilayer ceramic capacitor 1 is accommodated in taping 20, to thereby fabricate the series of multilayer ceramic capacitors 2. Then, a direction of stack of multilayer ceramic capacitors 1 accommodated in the series of multilayer ceramic capacitors 2 is identified. Consequently, a ratio of alignment of multilayer ceramic capacitor 1 is checked, and when multilayer ceramic capacitor 1 of which direction of stack is not desirable is detected, that multilayer ceramic capacitor 1 is marked or excluded.

Method of Identifying Direction

A method of identification of a direction of multilayer ceramic capacitor 1 carried out by direction identification portion 36 will now be described. In the description below, a capacitor of which direction of stack is perpendicular to a direction of a magnetic flux is defined as a "horizontal product" (because internal electrodes are horizontal to a bottom surface of accommodation chamber 21 as a multilayer ceramic capacitor) and a capacitor in which a direction of stack is in parallel thereto is defined as a "perpendicular product" (because internal electrodes are perpendicular to the bottom surface of accommodation chamber 21 as a multilayer ceramic capacitor).

Figure 6:
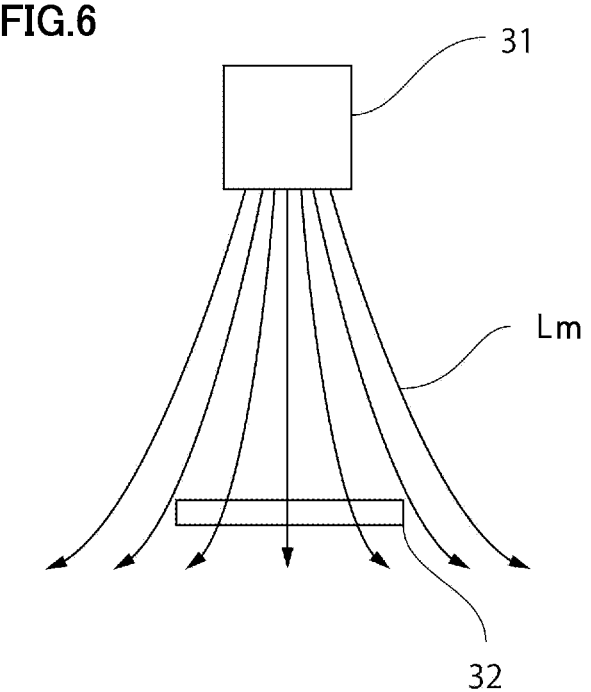
FIG. 6 is a schematic diagram of magnetic lines of force in a case that no multilayer ceramic capacitor is present between a magnetism generator and a magnetic flux density measurement instrument.

Initially, principles of the method of identifying a direction in the present embodiment will be described with reference to FIGS. 6 to 8. For example, as shown in FIG. 6, while no multilayer ceramic capacitor 1 is located between magnetism generator 31 and magnetic flux density measurement instrument 32, an interval among magnetic lines of force Lm which pass through magnetic flux density measurement instrument 32 is widest, or in other words, the number of magnetic lines of force Lm per unit area is small, and hence a magnetic flux density is low in value.

Figure 7:
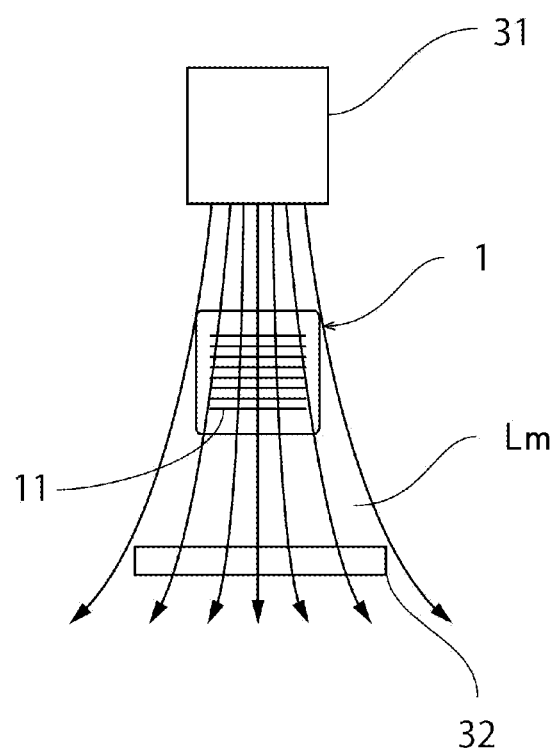
FIG. 7 is a schematic diagram of magnetic lines of force in a case that a multilayer ceramic capacitor is located between a magnetism generator and a magnetic flux density measurement instrument such that internal electrodes are perpendicular to a direction of a magnetic flux (internal electrodes are horizontal to a bottom surface as a capacitor).
Figure 8:
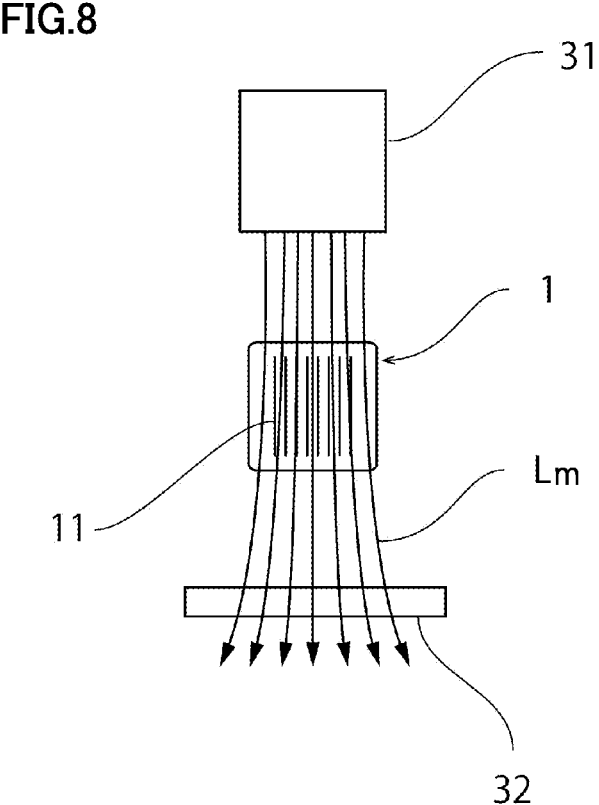
FIG. 8 is a schematic diagram of magnetic lines of force in a case that a multilayer ceramic capacitor is located between a magnetism generator and a magnetic flux density measurement instrument such that internal electrodes are horizontal to a direction of a magnetic flux (internal electrodes are perpendicular to a bottom surface as a capacitor).

As shown in FIGS. 7 and 8, in a case that multilayer ceramic capacitor 1 is located between magnetism generator 31 and magnetic flux density measurement instrument 32, an interval among magnetic lines of force Lm which pass through magnetic flux density measurement instrument 32 is narrower than in the case that no multilayer ceramic capacitor 1 is present. In the case that multilayer ceramic capacitor 1 is located between magnetism generator 31 and magnetic flux density measurement instrument 32, the number of magnetic lines of force Lm per unit area is greater than in the case that no multilayer ceramic capacitor 1 is present. An interval among magnetic lines of force Lm which pass through magnetic flux density measurement instrument 32 is narrower in a case that the direction of stack shown in FIG. 8 is in parallel to a direction of a magnetic flux (the internal electrodes are perpendicular to the bottom surface as a capacitor) than in a case that the direction of stack is perpendicular shown in FIG. 7 (the internal electrodes are horizontal to the bottom surface as a capacitor). The number of magnetic lines of force Lm per unit area is greater when the direction of stack is in parallel to a direction of a magnetic flux shown in FIG. 8.

Figure 9:
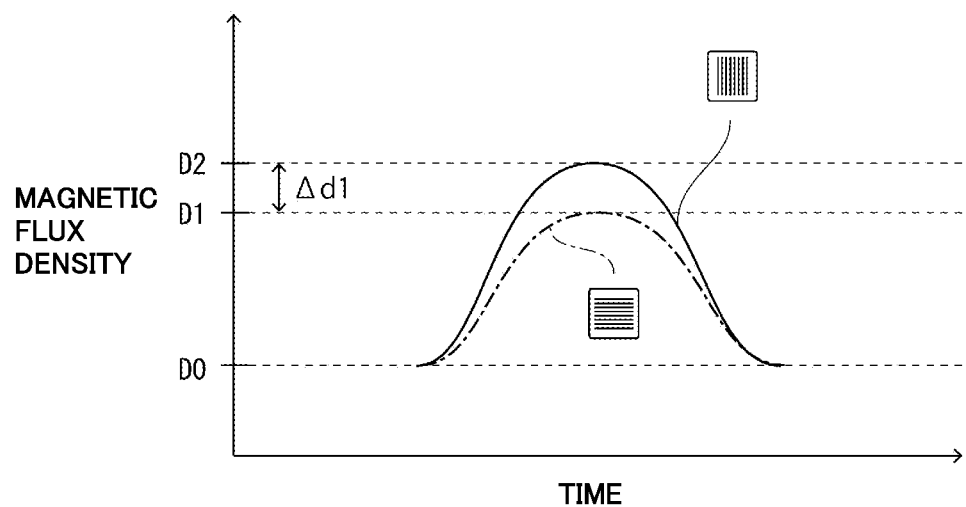
FIG. 9 is a schematic graph showing a magnetic flux density of a horizontal product and a perpendicular product.
Figure 10:
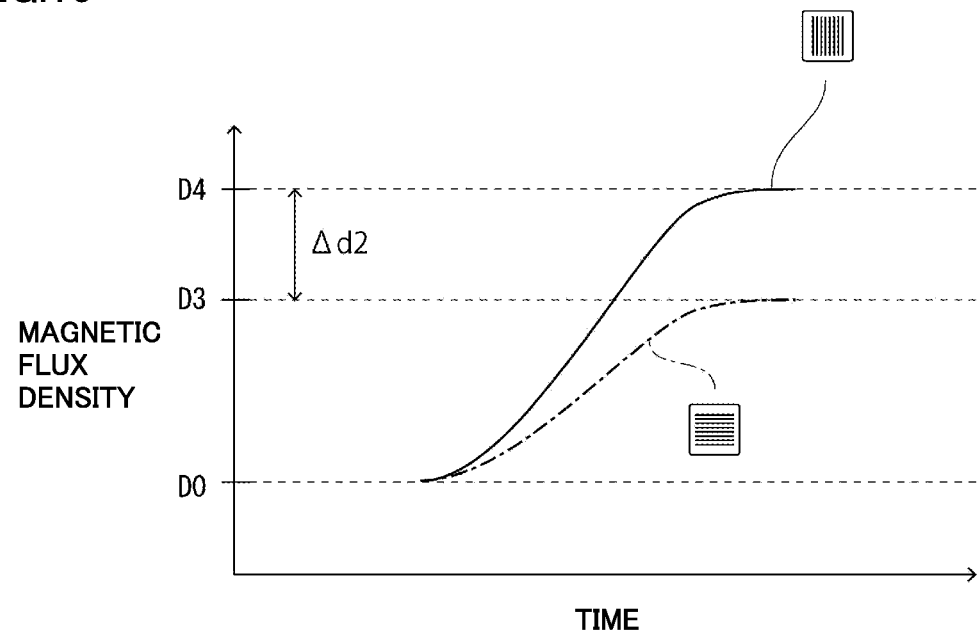
FIG. 10 is a schematic graph showing an integral value of a magnetic flux density of a horizontal product and a perpendicular product.

Therefore, as shown in FIG. 9, a measured magnetic flux density is higher when the direction of stack is in parallel to the direction of the magnetic flux than when the direction of stack is perpendicular. As shown in FIG. 10, an integral value of the measured magnetic flux density is higher when the direction of stack is in parallel to the direction of the magnetic flux than when the direction of stack is perpendicular.

Therefore, for example, a direction of stack of multilayer ceramic capacitor 1 can be identified based on a maximum value for a measured magnetic flux density. For example, a direction of stack of multilayer ceramic capacitor 1 can be identified based on an integral value of a measured magnetic flux density.

From a point of view of more accurate identification of a direction of stack of multilayer ceramic capacitor 1, a direction of stack is preferably identified based on an integral value of a measured magnetic flux density. A difference Δd2 (D4−D3) (see FIG. 10) between an integral value D3 of a magnetic flux density of a horizontal product and an integral value D4 of a magnetic flux density of a perpendicular product is greater than a difference Δd1 (D2−D1) (see FIG. 9) between a maximum magnetic flux density D1 of the horizontal product and a maximum magnetic flux density D2 of the perpendicular product. Therefore, accuracy in identification is higher in identification of a direction of multilayer ceramic capacitor 1 based on Δd2 than in identification of a direction of multilayer ceramic capacitor 1 based on Δd1. For example, even when a maximum value for a magnetic flux density may vary due to variation in position at the time of detection of multilayer ceramic capacitor 1, a direction of stack of multilayer ceramic capacitor 1 can accurately be identified by using an integral value of a magnetic flux density.

When a direction of stack of multilayer ceramic capacitor 1 is identified by using an integral value of a magnetic flux density, it is not necessary to detect a maximum value for a magnetic flux density. Therefore, a distance between magnetism generator 31 and magnetic flux density measurement instrument 32 can be greater. Therefore, lowering in accuracy in identification of a direction involved with variation in position of multilayer ceramic capacitor 1 at the time of measurement of a magnetic flux density of multilayer ceramic capacitor 1 can be suppressed.

In particular, when the number of stacked internal electrodes 11 and 12 is small, Δd1 tends to be small and a difference between Δd2 and Δd1 (Δd2−Δd1) tends to be great. Therefore, when the number of stacked internal electrodes 11 and 12 is small, preferably, a direction of stack is identified by using an integral value of a magnetic flux density rather than a maximum value for a magnetic flux density. Specifically, identification of a direction of stack by using an integral value of a magnetic flux density is more suitable for multilayer ceramic capacitor 1 in which the number of stacked internal electrodes 11 and 12 is not greater than 100.

Another example of a preferred embodiment of the present disclosure will be described below. In the description below, a member having a function substantially common to that in the first embodiment has a common character allotted and the description will not be repeated.

Second Embodiment

In the first embodiment, an example in which a magnetic flux density of multilayer ceramic capacitors 1 accommodated in a series of multilayer ceramic capacitors 2 is measured has been described, however, the present disclosure is not limited thereto.

Figure 11:
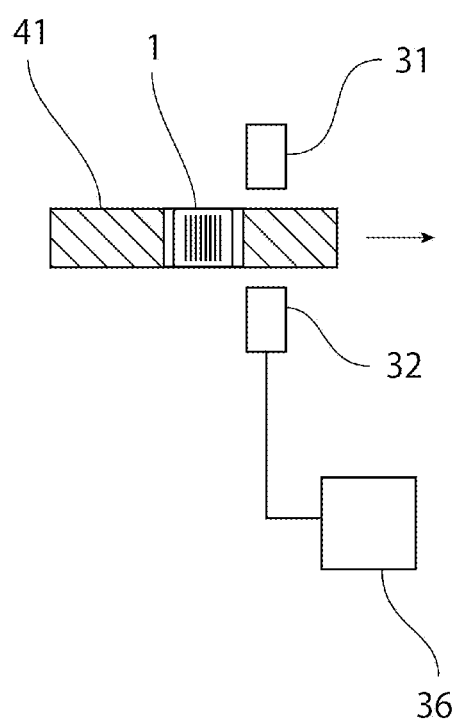
FIG. 11 is a schematic side view showing a main portion of an apparatus identifying a direction of a multilayer ceramic capacitor in a second embodiment.

For example, as shown in FIG. 11, a direction of stack of multilayer ceramic capacitor 1 may be identified while a transportation apparatus 41 transports multilayer ceramic capacitor 1 not accommodated in taping, between magnetism generator 31 and magnetic flux density measurement instrument 32. After multilayer ceramic capacitor 1 passes between magnetism generator 31 and magnetic flux density measurement instrument 32, a direction of stack may be aligned by turning multilayer ceramic capacitor 1, and multilayer ceramic capacitor 1 of which direction of stack is not desirable may be excluded.

Third Embodiment

Figure 12:
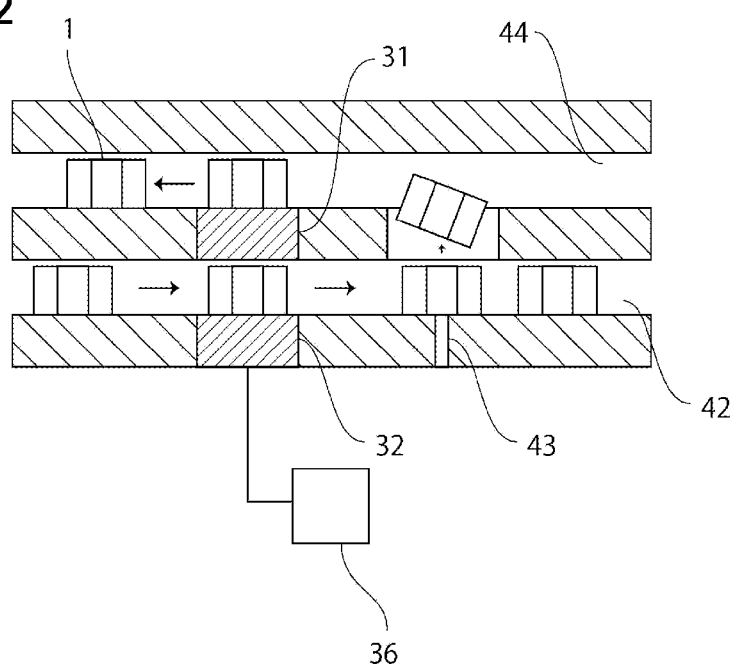
FIG. 12 is a schematic side view showing a main portion of an apparatus identifying a direction of a multilayer ceramic capacitor in a third embodiment.

FIG. 12 is a schematic side view showing a main portion of an apparatus identifying a direction of a multilayer ceramic capacitor in a third embodiment. In the present embodiment, magnetism generator 31 and magnetic flux density measurement instrument 32 are provided in a transportation path 42. To transportation path 42, a plurality of multilayer ceramic capacitors 1 are supplied in one line (along one direction) by a feeder such as a linear feeder. Stack ceramic capacitor 1 of which direction of stack has been determined as inappropriate is blown off from transportation path 42 to a transportation path 44 by a gas injected from a blowout hole 43. Blown multilayer ceramic capacitor 1 is recovered or discarded via transportation path 44.

Stack ceramic capacitor 1 transported over transportation path 42 may be accommodated in taping, for example, by a taping accommodation machine, or for example, may be mounted on a mount substrate by a mounting machine.

Fourth Embodiment

Figure 13:
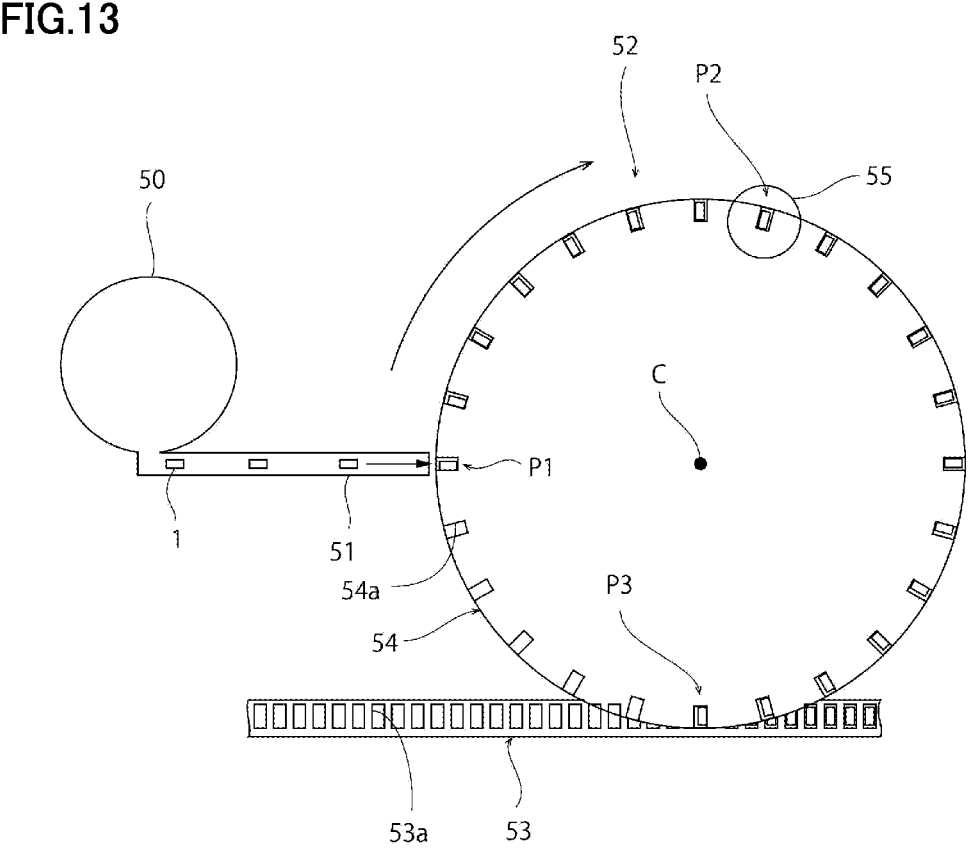
FIG. 13 is a schematic plan view showing an apparatus identifying a direction of a multilayer ceramic capacitor in a fourth embodiment.

FIG. 13 is a schematic plan view showing an apparatus identifying a direction of a multilayer ceramic capacitor in a fourth embodiment. A direction identification apparatus in the fourth embodiment forms a part of an apparatus manufacturing a series of tape-packaged electronic components.

In the present embodiment, a ball feeder 50 is provided in the apparatus manufacturing a series of tape-packaged electronic components. Ball feeder 50 accommodates a plurality of multilayer ceramic capacitors 1. Ball feeder 50 successively supplies electronic components to a linear feeder 51 by vibrating.

Linear feeder 51 transports multilayer ceramic capacitor 1 supplied by vibration. Linear feeder 51 supplies multilayer ceramic capacitor 1 to a transportation apparatus 52. Transportation apparatus 52 transports multilayer ceramic capacitor 1 to a carrier tape 53. Transportation apparatus 52 has a disc-shaped transportation table 54 which turns around a central axis C.

Specifically, in the present embodiment, transportation table 54 which is an annular rotor turns clockwise around central axis C. Transportation table 54 includes a plurality of recesses (accommodation portions) 54a. A plurality of recesses 54a are provided in one line around an outer circumference of the annular rotor at an interval from one another. At a position P1, multilayer ceramic capacitor 1 is thrown into recess 54a in transportation table 54 from linear feeder 51. Stack ceramic capacitor 1 thrown into recess 54a at position P1 is transported along a circumferential direction around central axis C as transportation table 54 turns.

Stack ceramic capacitor 1 is transported to a position P3. At position P3, multilayer ceramic capacitor 1 is accommodated in an accommodation chamber 53a in carrier tape 53 from transportation table 54. At a position P2 located between position P1 and position P3 in a transportation path, a direction identification apparatus 55 is provided. Direction identification apparatus 55 includes magnetism generator 31 and magnetic flux density measurement instrument 32.

This direction identification apparatus 55 identifies a direction of stack of multilayer ceramic capacitor 1. After multilayer ceramic capacitor 1 passes between magnetism generator 31 and magnetic flux density measurement instrument 32, a direction of stack may be aligned by turning multilayer ceramic capacitor 1 or multilayer ceramic capacitor 1 of which direction of stack is not desirable may be excluded. In the present embodiment as well, before multilayer ceramic capacitor 1 is accommodated in taping, a direction of stack of multilayer ceramic capacitor 1 can be identified.

Fifth Embodiment

Figure 14:
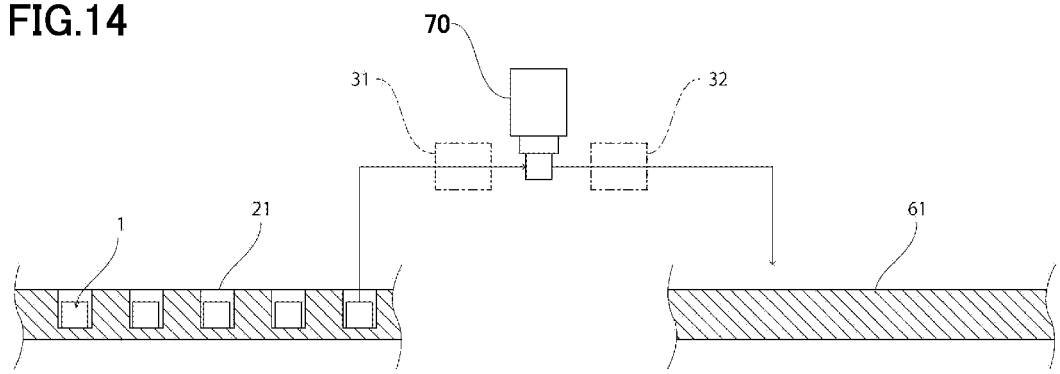
FIG. 14 is a schematic side view showing an apparatus identifying a direction of a multilayer ceramic capacitor in a fifth embodiment.

FIG. 14 is a schematic side view showing an apparatus identifying a direction of a multilayer ceramic capacitor in a fifth embodiment. The direction identification apparatus shown in FIG. 14 may include, for example, magnetism generator 31 and magnetic flux density measurement instrument 32 arranged with a mounter 70 for mounting on a mount substrate 61 being interposed. In this case, a direction of stack of multilayer ceramic capacitor 1 can be determined before mounting. Mounter 70 may include, for example, a suction nozzle.

First Experimental Example

Figure 15:
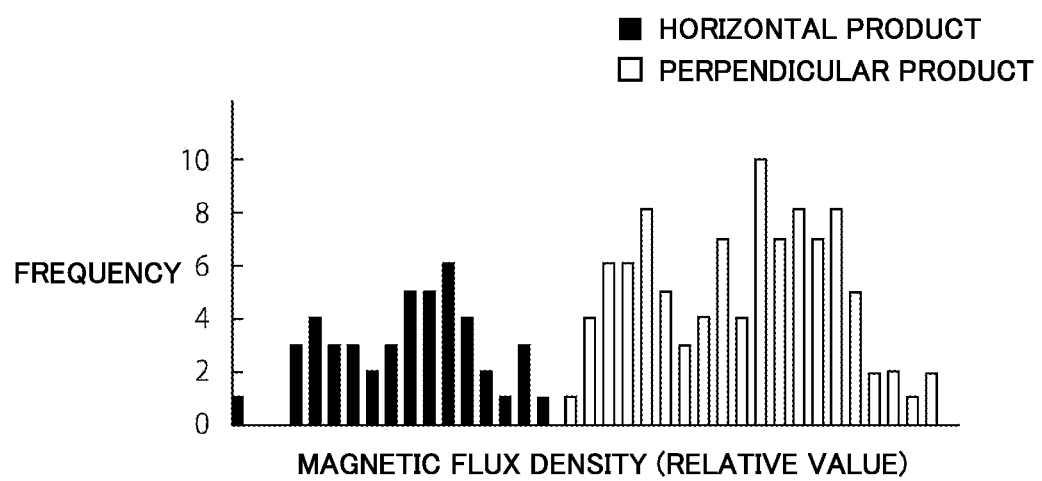
FIG. 15 is a histogram of a maximum value for a magnetic flux density in a first experimental example.
Figure 16:
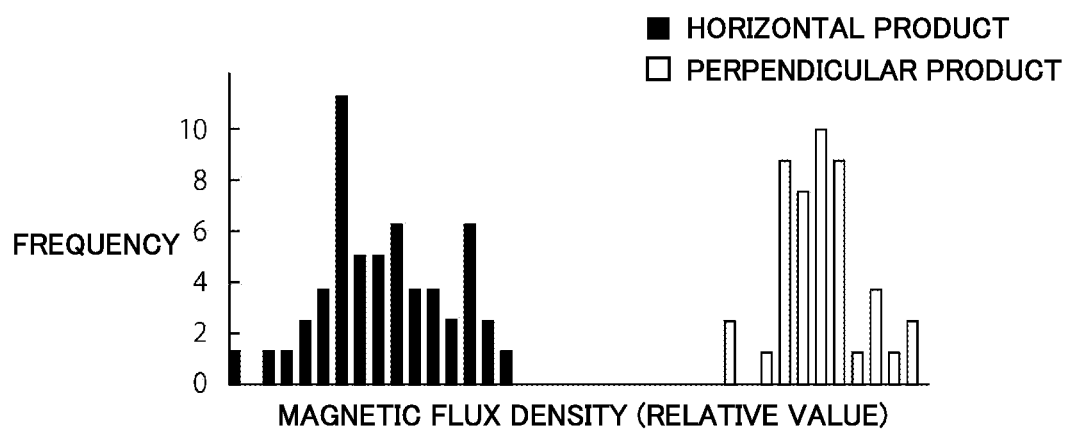
FIG. 16 is a histogram of an integral value of a magnetic flux density in the first experimental example.

One hundred and fifty stack capacitors having a design parameter below were prepared. Then, a maximum value for a magnetic flux density was measured with the stack capacitors being set as horizontal products, and thereafter, a maximum value for a magnetic flux density was measured with the stack capacitors being set as perpendicular products. FIG. 15 shows the results. An integral value of a magnetic flux density was measured with the stack capacitors being set as horizontal products, and thereafter, an integral value of a magnetic flux density was measured with the stack capacitors being set as perpendicular products. FIG. 16 shows the results. In each of FIGS. 15 and 16, the ordinate represents a frequency and the abscissa represents a magnetic flux density.

It can be seen from the results shown in FIG. 15 that a difference in magnetic flux density between the horizontal products and the perpendicular products is less likely when a maximum value for a magnetic flux density was measured. On the other hand, it can be seen that a difference in magnetic flux density between the horizontal products and the perpendicular products is more likely when an integral value of a magnetic flux density was measured. It can be seen from this result that a direction of a multilayer ceramic capacitor can accurately be identified by using an integral value of a magnetic flux density.

In the present experimental example, the multilayer ceramic capacitor had a size of 1 mm×0.5 mm×0.5 mm, an electrode mainly composed of nickel was adopted as an internal electrode, the number of stacked internal electrodes was set to 40, and the multilayer ceramic capacitor had a capacitance of 0.1 µF.

Sixth Embodiment

Figure 17:
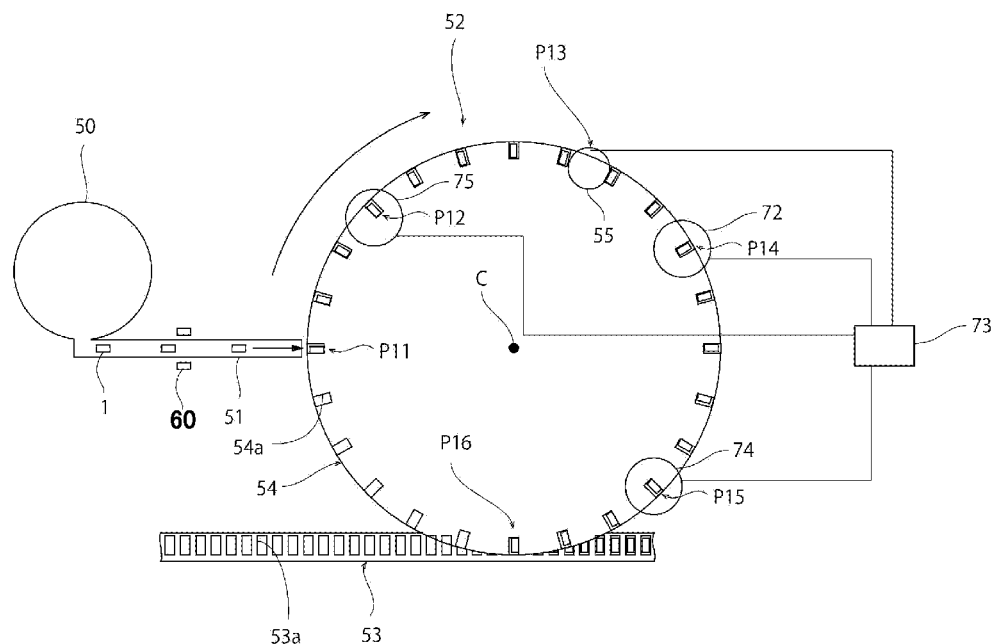
FIG. 17 is a schematic plan view of an apparatus identifying a direction of a multilayer ceramic capacitor in a sixth embodiment.

FIG. 17 is a schematic plan view showing an apparatus identifying a direction of multilayer ceramic capacitor 1 in a sixth embodiment.

As shown in FIG. 17, linear feeder 51 supplies multilayer ceramic capacitor 1 to rotary transportation apparatus 52. Transportation apparatus 52 transports multilayer ceramic capacitor 1 to carrier tape 53. Transportation apparatus 52 includes disc-shaped transportation table 54 which turns around central axis C and a transportation stage 71 (see FIG. 18) on which transportation table 54 is arranged. As shown in FIG. 17, linear feeder 51 is provided with a magnetism generator 60 generating magnetism, and multilayer ceramic capacitor 1 is magnetized as multilayer ceramic capacitor 1 passes before this magnetism generator 60. Magnetism generator 60 also functions to align orientations of internal electrodes 11 and 12 by turning multilayer ceramic capacitor 1 with magnetic force.

Figure 18:
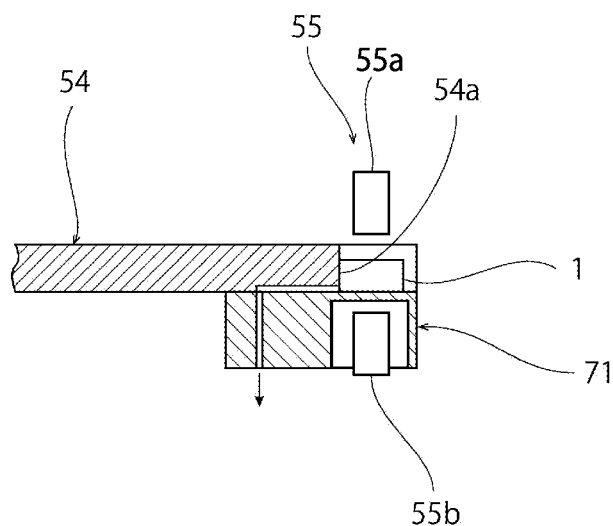
FIG. 18 is a cross-sectional view of a main portion of a direction identification apparatus in FIG. 17.

Transportation table 54 includes a plurality of recesses 54a in an outer circumferential surface and the plurality of recesses 54a are provided along the circumferential direction of transportation table 54 at regular intervals. The plurality of recesses 54a extend from the outer circumferential surface of transportation table 54 toward central axis C and penetrates from one main surface to the other main surface of transportation table 54. As shown in FIG. 18, transportation table 54 is provided on transportation stage 71, and this transportation stage 71 closes a lower side of recess 54a.

As shown in FIG. 17, a capacitance measurement portion 75 is arranged at a position P12 located in a transportation path from a position P11 to a position P16. This capacitance measurement portion 75 measures a capacitance of multilayer ceramic capacitor 1 accommodated in recess 54a. A measured capacitance of multilayer ceramic capacitor 1 is output to a control unit 73.

A magnetic flux density measurement portion implementing direction identification apparatus 55 is provided at a position P13 located between position P12 and position P16. The magnetic flux density measurement portion measures a magnetic flux density at the time when multilayer ceramic capacitor 1 passes, in order to identify a direction of stack of multilayer ceramic capacitor 1. As shown in FIG. 18, the magnetic flux density measurement portion has a magnetism generator 55a and a magnetic flux density measurement instrument 55b. Magnetism generator 55a is opposed to magnetic flux density measurement instrument 55b. Stack ceramic capacitor 1 transported by transportation apparatus 52 passes between magnetism generator 55a and magnetic flux density measurement instrument 55b. Transportation table 54 and transportation stage 71 which transport multilayer ceramic capacitor 1 are located between magnetism generator 55a and magnetic flux density measurement instrument 55b.

A density of a magnetic flux which passes from magnetism generator 55a through multilayer ceramic capacitor 1 and reaches magnetic flux density measurement instrument 55b is different between a case that a direction of stack is perpendicular to a direction of alignment of magnetism generator 55a and magnetic flux density measurement instrument 55b and a case that the direction of stack is in parallel thereto. Therefore, by detecting a magnetic flux density at the time when multilayer ceramic capacitor 1 passes between magnetism generator 55a and magnetic flux density measurement instrument 55b with magnetic flux density measurement instrument 55b, a direction of stack of multilayer ceramic capacitor 1 can be identified. Magnetic flux density measurement instrument 55b outputs the detected magnetic flux density to control unit 73 serving as the direction identification portion. Control unit 73 performs operation processing of the measured magnetic flux density as appropriate and finds, for example, an integral value of a magnetic flux density described above.

From a point of view of more reliable identification of a direction of stack of multilayer ceramic capacitor 1, transportation table 54 is preferably formed of a non-magnetic element such as stainless steel, aluminum, plastic, or ceramics. Transportation stage 71 is preferably formed of a non-magnetic element such as stainless steel, aluminum, plastic, or ceramics. Among these, transportation table 54 and transportation stage 71 are more preferably formed of zirconia which is excellent also in wear resistance. In such a case, a density of a magnetic flux which has passed through multilayer ceramic capacitor 1 can more accurately be measured.

As shown in FIG. 17, an image pick-up portion 72 is provided at a position P14 located between position P13 and position P16 in the transportation path. Image pick-up portion 72 picks up an image of multilayer ceramic capacitor 1 from above. The picked up image is output to control unit 73.

A screening portion 74 is provided at a position P15 located between position P14 and position P16 in the transportation path. Screening portion 74 is connected to control unit 73 and screens multilayer ceramic capacitor 1 based on an instruction from control unit 73. Specifically, control unit 73 determines whether or not a capacitance output from capacitance measurement portion 75 is within a range of a predetermined capacitance (specifications of a capacitance). Control unit 73 determines whether or not a direction of stack specified based on a magnetic flux density matches with a predetermined direction. Control unit 73 determines whether or not appearance of multilayer ceramic capacitor 1 is dissatisfactory based on an image output from image pick-up portion 72. Control unit 73 recognizes multilayer ceramic capacitor 1 which fails to satisfy even one of the three conditions above as a defective product and has the multilayer ceramic capacitor removed.

Arrangement of each of capacitance measurement portion 75, the magnetic flux density measurement portion (direction identification apparatus 55), image pick-up portion 72, and screening portion 74 in the present embodiment will more specifically be described. Transportation table 54 performs what is called an intermittent operation in which rotary motion and stop are repeated at a certain interval. A position of each of capacitance measurement portion 75, image pick-up portion 72, and screening portion 74 is superimposed on a position of recess 54a while transportation table 54 remains stopped. On the other hand, a position of the magnetic flux density measurement portion is superimposed on a position where recess 54a is passing during rotary motion of transportation table 54.

Namely, when the positions of capacitance measurement portion 75, image pick-up portion 72, and screening portion 74 are superimposed on the positions of recesses 54a, respectively, the position of the magnetic flux density measurement portion (direction identification apparatus 55) and the position of recess 54a are not superimposed on each other. In contrast, when the position of the magnetic flux density measurement portion (direction identification apparatus 55) and the position of recess 54a are superimposed on each other, the positions of capacitance measurement portion 75, image pick-up portion 72, and screening portion 74 are not superimposed on the positions of recesses 54a, respectively.

The positions of capacitance measurement portion 75, image pick-up portion 72, screening portion 74, and the magnetic flux density measurement portion being superimposed on the positions of recesses 54a, respectively, means that a center of each of capacitance measurement portion 75, image pick-up portion 72, screening portion 74, and the magnetic flux density measurement portion is superimposed on a part of any recess 54a along the circumferential direction of transportation table 54.

For example, when N recesses 54a are arranged at regular intervals in transportation table 54 and transportation table 54 repeats rotary motion of (360/N) degrees and stops, positions of capacitance measurement portion 75, image pick-up portion 72, and screening portion 74 are each displaced by an integral multiple of (360/N) degrees from the center of rotation of transportation table 54. On the other hand, a position of the magnetic flux density measurement portion is different from a position resulting from displacement by an integral multiple of (360/N) degrees from arrangement of each of capacitance measurement portion 75, image pick-up portion 72, and screening portion 74.

In any form in the first to sixth embodiments described so far, an interval between adjacent multilayer ceramic capacitors 1 affects accuracy in identification of a direction of stack. A direction of stack is identified by finding a magnetic flux density at the time when multilayer ceramic capacitor 1 passes the magnetic flux density measurement portion. Therefore, when an interval between adjacent multilayer ceramic capacitors 1 is excessively narrow, a magnetic flux density is affected by adjacent multilayer ceramic capacitor 1 and accuracy in identification of a direction of stack lowers.

Therefore, an interval between adjacent multilayer ceramic capacitors 1 is preferably not less than ½ a dimension of magnetism generator 55a in a direction of passage of multilayer ceramic capacitor 1. Alternatively, an interval between adjacent multilayer ceramic capacitors 1 is preferably not smaller than a dimension of multilayer ceramic capacitor 1 in a direction of passage of multilayer ceramic capacitor 1.

In the first to sixth embodiments described so far, magnetism generator 31 and magnetic flux density measurement instrument 32 are arranged as being opposed to each other and multilayer ceramic capacitor 1 passes therebetween. In a seventh embodiment described next, however, arrangement of magnetism generator 31 and magnetic flux density measurement instrument 32 is different.

Seventh Embodiment

Figure 19:
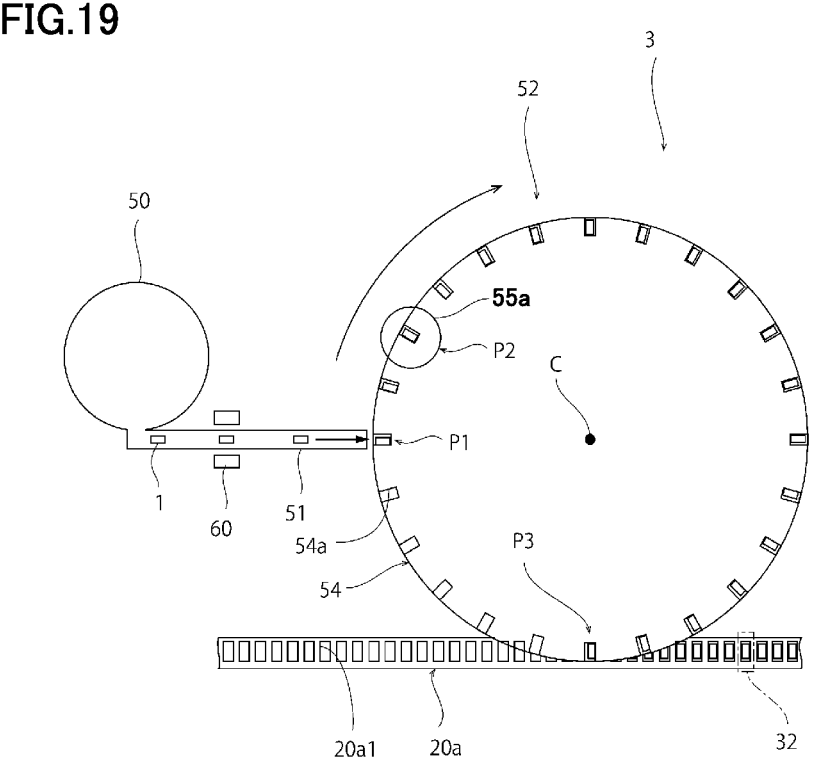
FIG. 19 is a schematic plan view of an apparatus manufacturing a series of multilayer ceramic capacitors in a seventh embodiment of the present disclosure.

As shown in FIG. 19, linear feeder 51 is provided with magnetism generator 60 generating magnetism. Stack ceramic capacitor 1 is magnetized as multilayer ceramic capacitor 1 passes before this magnetism generator 60. Stack ceramic capacitor 1 being magnetized means that a multilayer ceramic capacitor becomes magnetic.

Magnetism generator 60 also functions to align orientations of internal electrodes 11 and 12 in multilayer ceramic capacitor 1 transported by linear feeder 51. For example, when a direction of stack of internal electrodes 11 and 12 in multilayer ceramic capacitor 1 is in parallel to the horizontal direction, multilayer ceramic capacitor 1 is turned by 90° by magnetism generated form magnetism generator 60 such that the direction of stack of internal electrodes 11 and 12 is in parallel to a vertical direction. Thus, orientations of multilayer ceramic capacitors 1 which pass a portion where magnetism generator 60 is provided are aligned. Orientations of all multilayer ceramic capacitors 1 do not necessarily have to be aligned.

Magnetism generator 55a is arranged at position P2 located between position P1 and position P3 in the transportation path. This magnetism generator 55a further magnetizes multilayer ceramic capacitor 1. Therefore, magnetized multilayer ceramic capacitors 1 are accommodated in the series of multilayer ceramic capacitors 2. In the present embodiment, an example in which two magnetism generators of magnetism generator 55a and magnetism generator 60 are provided has been described. The present disclosure, however, is not limited to this construction. Only a single magnetism generator may be provided.

Figure 20:
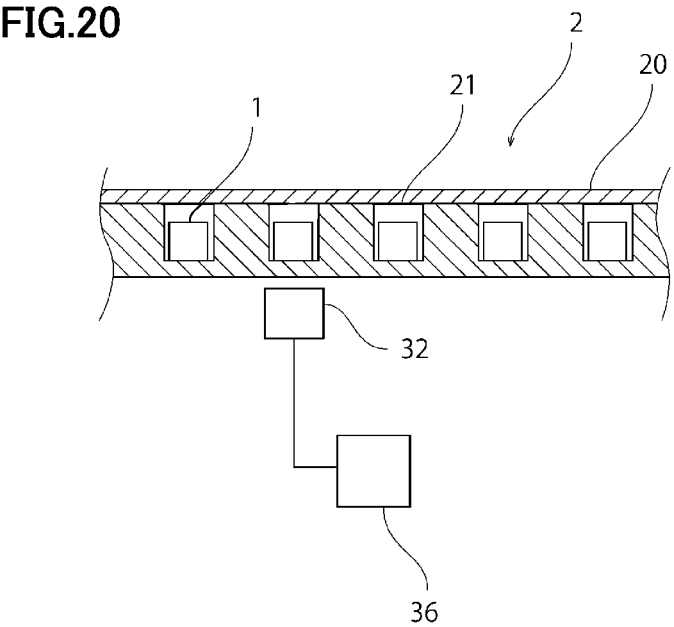
FIG. 20 is a simplified cross-sectional view of the series of multilayer ceramic capacitors in the seventh embodiment of the present disclosure.

As shown in FIG. 20, magnetic flux density measurement instrument 32 for measuring a magnetic flux density is provided below the series of multilayer ceramic capacitors 2. Specifically, magnetic flux density measurement instrument 32 successively measures a magnetic flux density at an interval approximately not less than 10 kHz and not more than 100 kHz.

In the present embodiment, magnetism generators 55a and 60 magnetize multilayer ceramic capacitor 1 (a magnetization step). Then, magnetic flux density measurement instrument 32 is used to measure a density of a magnetic flux generated from magnetized multilayer ceramic capacitor 1 (a magnetic flux density measurement step). In the magnetic flux density measurement step, a magnetic flux density at the time when magnetized multilayer ceramic capacitor 1 passes before magnetic flux density measurement instrument 32 is preferably measured.

Then, direction identification portion 36 identifies a direction of stack of internal electrodes 11 and 12 in multilayer ceramic capacitor 1 based on a result of measurement of a magnetic flux density (a stack direction identification step). A direction of multilayer ceramic capacitor 1 can be identified based on a maximum value or an integral value of a magnetic flux density measured here. Consequently, for example, a ratio of alignment of multilayer ceramic capacitors 1 is checked, and when multilayer ceramic capacitor 1 of which direction is different from a desired direction is detected, that multilayer ceramic capacitor 1 is marked or excluded.

Figure 21:
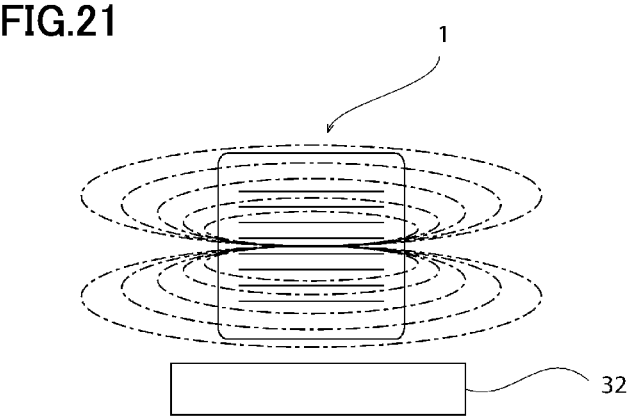
FIG. 21 is a schematic diagram representing magnetic lines of force of a multilayer ceramic capacitor in a case that internal electrodes are in parallel to a magnetic flux density measurement instrument.
Figure 22:
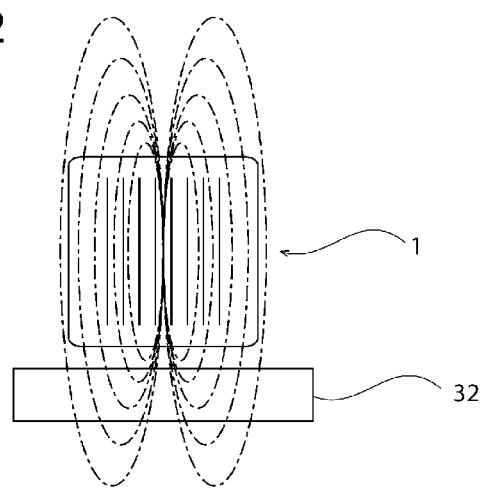
FIG. 22 is a schematic diagram representing magnetic lines of force of a multilayer ceramic capacitor in a case that internal electrodes are perpendicular to a magnetic flux density measurement instrument.

Principles of the method of identifying a direction in the present embodiment will be described with reference to FIGS. 21 and 22. While no multilayer ceramic capacitor 1 is present before magnetic flux density measurement instrument 32, magnetic flux density measurement instrument 32 does not substantially measure a magnetic flux. On the other hand, as shown in FIGS. 21 and 22, when magnetized multilayer ceramic capacitor 1 is located before magnetic flux density measurement instrument 32, magnetic lines of force from multilayer ceramic capacitor 1 pass through magnetic flux density measurement instrument 32. Therefore, magnetic flux density measurement instrument 32 measures a magnetic flux. Consequently, as shown in FIGS. 9 and 10, a maximum value and an integral value of a magnetic flux density are different depending on a direction of stack of multilayer ceramic capacitor 1.

In the present embodiment, since multilayer ceramic capacitor 1 is magnetized in advance, it is not necessarily required to arrange magnetism generators 55a and 60 and magnetic flux density measurement instrument 32 as being opposed to each other. Therefore, a degree of freedom in arrangement of magnetism generators 55a and 60 and magnetic flux density measurement instrument 32 is high, and restriction in terms of a structure on a direction identification apparatus and a manufacturing apparatus is lessened. Therefore, a direction identification apparatus and a manufacturing apparatus can be, for example, smaller in size. After a direction of multilayer ceramic capacitor 1 is identified, magnetized multilayer ceramic capacitor 1 may be subjected to a demagnetization process.

Eighth and Ninth Embodiments

Figure 23:
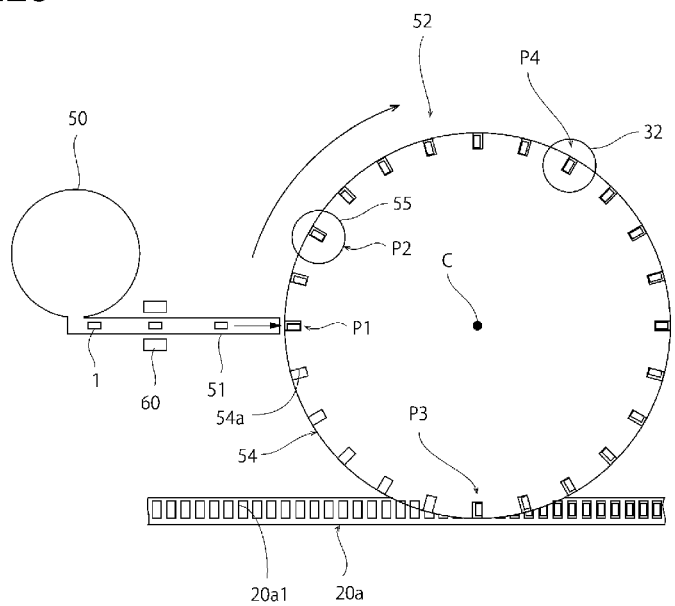
FIG. 23 is a schematic plan view showing a main portion of an apparatus identifying a direction of a multilayer ceramic capacitor in an eighth embodiment.
Figure 24:
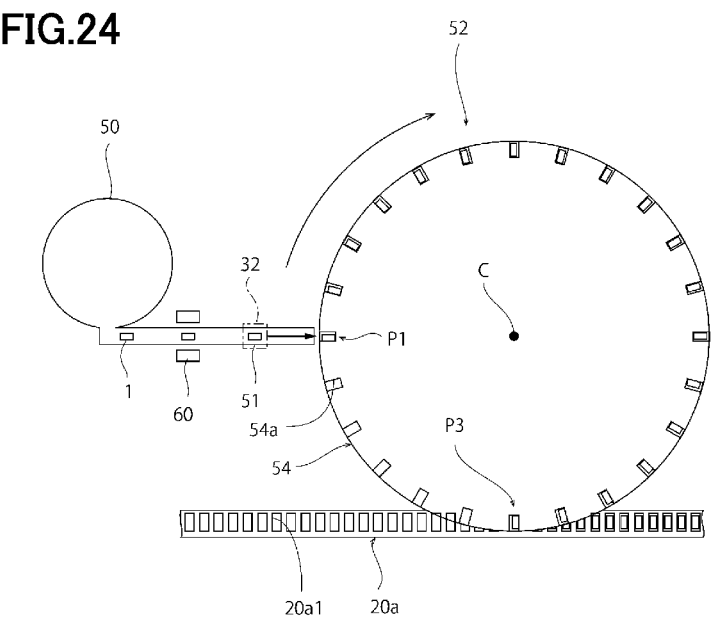
FIG. 24 is a schematic plan view showing a main portion of an apparatus identifying a direction of a multilayer ceramic capacitor in a ninth embodiment.

FIG. 23 is a schematic plan view showing a main portion of an apparatus identifying a direction of a multilayer ceramic capacitor in an eighth embodiment. FIG. 24 is a schematic plan view showing a main portion of an apparatus identifying a direction of a multilayer ceramic capacitor in a ninth embodiment.

In the seventh embodiment, an example in which magnetic flux density measurement instrument 32 identifies a direction of multilayer ceramic capacitors 1 accommodated in the series of multilayer ceramic capacitors 2 has been described, however, the present disclosure is not limited thereto.

For example, as shown in FIG. 23, magnetic flux density measurement instrument 32 may be provided in transportation apparatus 52. Specifically, in the eighth embodiment, magnetic flux density measurement instrument 32 is arranged at position P4 of transportation apparatus 52. Alternatively, for example, as in the ninth embodiment shown in FIG. 24, magnetic flux density measurement instrument 32 may be provided in linear feeder 51. Therefore, a direction of multilayer ceramic capacitor 1 can be identified during transportation by transportation apparatus 52, before accommodation in the series of multilayer ceramic capacitors 2.

In the eighth and ninth embodiments, a screening portion screening multilayer ceramic capacitor 1 of which direction is not in a desired direction of stack and an alignment portion turning multilayer ceramic capacitor 1 and setting the multilayer ceramic capacitor to a desired direction of stack may further be provided between position P4 and position P3. The screening portion may remove multilayer ceramic capacitor 1 in which a direction of stack of internal electrodes 11 and 12 is undesirable.

Second Experimental Example

FIRST EXAMPLE

Six multilayer ceramic capacitors having a design parameter below were prepared. As shown in FIG. 19, only magnetism generator 60, which was constituted of a pair of permanent magnets opposed to each other with linear feeder 51 being interposed, magnetized the multilayer ceramic capacitors. A magnetic flux density of three of the six samples was measured as the samples were arranged such that internal electrodes were in parallel to the magnetic flux density measurement instrument, and a magnetic flux density of the remaining three was measured as the samples were arranged such that internal electrodes were perpendicular to the magnetic flux density measurement instrument. Table 1 shows a maximum value for a measured magnetic flux density. In Table 1, a sample with an annotation "horizontal" refers to a sample of which magnetic flux density was measured with internal electrodes being arranged to be in parallel to the magnetic flux density measurement instrument. In Table 1, a sample with an annotation "perpendicular" refers to a sample of which magnetic flux density was measured with internal electrodes being arranged to be perpendicular to the magnetic flux density measurement instrument.

SECOND EXAMPLE

Six multilayer ceramic capacitors used in the first example were demagnetized such that a density of a magnetic flux was not higher than 0.05 mT, and thereafter they were again used as samples in the present second example. In the second example, two magnetism generators of magnetism generator 60 constructed as in the first example and magnetism generator 55a provided in transportation apparatus 52 and formed from a permanent magnet magnetized the multilayer ceramic capacitors. A magnetic flux density of three of the six samples was measured as the samples were arranged such that internal electrodes were in parallel to the magnetic flux density measurement instrument, and a magnetic flux density of the remaining three was measured as the samples were arranged such that internal electrodes were perpendicular to the magnetic flux density measurement instrument. Table 1 shows a maximum value for a measured magnetic flux density. Table 1 shows a maximum value for a measured magnetic flux density.

In the present experimental example, the multilayer ceramic capacitor had a size of 1.15 mm×0.65 mm×0.65 mm, an electrode mainly composed of nickel was adopted as an internal electrode, the number of stacked internal electrodes was set to 430, and the multilayer ceramic capacitor had a capacitance of 10 μF.

TABLE 1

| Maximum Value for Magnetic Flux Density (mT) | First Example | Second Example |
| --- | --- | --- |
| Sample 1 (Horizontal) | 0.108 | 0.309 |
| Sample 2 (Horizontal) | 0.134 | 0.317 |
| Sample 3 (Horizontal) | 0.134 | 0.316 |
| Sample 4 (Perpendicular) | 0.268 | 0.416 |
| Sample 5 (Perpendicular) | 0.238 | 0.420 |
| Sample 6 (Perpendicular) | 0.216 | 0.414 |

It can be seen from the results shown in Table 1 that a direction of a multilayer ceramic capacitor can be identified by measuring a magnetic flux density of a multilayer ceramic capacitor magnetized in advance. By carrying out magnetization twice as in the second example, a measured value (a maximum value and an integral value) of a magnetic flux density of a multilayer ceramic capacitor is greater and identification of a direction is further facilitated.

Though the embodiments of the present disclosure have been described, it should be understood that the embodiments disclosed herein are illustrative and non-restrictive in every respect. The scope of the present disclosure is defined by the terms of the claims, and is intended to include any modifications within the scope and meaning equivalent to the terms of the claims.

What is claimed is:

1. A method of identifying a direction of stack of a multilayer ceramic capacitor including a plurality of stacked internal electrodes, comprising the steps of:
   transporting a plurality of multilayer ceramic capacitors in one line before each of a magnetism generator and a magnetic flux density measurement instrument;
   measuring a magnetic flux density with said magnetic flux density measurement instrument when each of said plurality of multilayer ceramic capacitors passes before said magnetic flux density measurement instrument; and
   identifying said direction of stack based on said magnetic flux density measured in said step of measuring a magnetic flux density.

2. The method of identifying a direction of a multilayer ceramic capacitor according to claim 1, wherein
   in said step of identifying said direction of stack, an integral value of the magnetic flux density is calculated based on said magnetic flux density measured in said step of measuring a magnetic flux density and said direction of stack is identified based on the integral value of said magnetic flux density.

3. The method of identifying a direction of a multilayer ceramic capacitor according to claim 1, wherein
   said magnetism generator and said magnetic flux density measurement instrument are opposed to each other, and
   in said step of measuring a magnetic flux density, said magnetic flux density measurement instrument measures a density of a magnetic flux generated from said magnetism generator when each of said plurality of multilayer ceramic capacitors passes between said magnetism generator and said magnetic flux density measurement instrument.

4. The method of identifying a direction of a multilayer ceramic capacitor according to claim 1, wherein
   said magnetism generator is arranged upstream of said magnetic flux density measurement instrument in a direction of transportation of said plurality of multilayer ceramic capacitors, and
   the method further comprises the step of magnetizing each of said plurality of multilayer ceramic capacitors before said step of measuring a magnetic flux density.

5. The method of identifying a direction of a multilayer ceramic capacitor according to claim 1, wherein
   in said step of transporting a plurality of multilayer ceramic capacitors, said plurality of multilayer ceramic capacitors are transported to pass through a linear transportation path, and
   in said step of measuring a magnetic flux density, said magnetic flux density measurement instrument measures the magnetic flux density when said plurality of multilayer ceramic capacitors pass before said magnetic flux density measurement instrument as said plurality of multilayer ceramic capacitors pass through said linear transportation path.

6. The method of identifying a direction of a multilayer ceramic capacitor according to claim 1, wherein
   in said step of transporting a plurality of multilayer ceramic capacitors, said plurality of multilayer ceramic capacitors are transported while said plurality of multilayer ceramic capacitors are accommodated in a plurality of accommodation portions provided along an outer circumference of an annular rotor, respectively, and
   in said step of measuring a magnetic flux density, said magnetic flux density measurement instrument measures the magnetic flux density when said plurality of multilayer ceramic capacitors pass before said magnetic flux density measurement instrument while said plurality of multilayer ceramic capacitors are accommodated in said plurality of accommodation portions, respectively.

7. The method of identifying a direction of a multilayer ceramic capacitor according to claim 1, wherein
   in said step of transporting a plurality of multilayer ceramic capacitors, said plurality of multilayer ceramic capacitors are transported while said plurality of multilayer ceramic capacitors are accommodated in a plurality of cavities, respectively, which are provided in a taping, and
   in said step of measuring a magnetic flux density, said magnetic flux density measurement instrument measures the magnetic flux density when said plurality of multilayer ceramic capacitors pass before said magnetic flux density measurement instrument while said plurality of multilayer ceramic capacitors are accommodated in said plurality of cavities, respectively.

8. A method of manufacturing a series of multilayer ceramic capacitors, comprising the steps of:
 identifying said direction of stack with the method of identifying a direction of a multilayer ceramic capacitor according to claim 1; and
 accommodating a plurality of multilayer ceramic capacitors identical in said direction of stack in a plurality of cavities provided in a taping, respectively.

* * * * *